US012397034B2

(12) United States Patent
Lin et al.

(10) Patent No.: US 12,397,034 B2
(45) Date of Patent: Aug. 26, 2025

(54) PHARMACEUTICAL COMPOSITION FOR PROMOTING NEUROGENESIS AND METHOD FOR PROMOTING NEUROGENESIS AND INHIBITING SENESCENCE OF BRAIN NEURONS

(71) Applicants: China Medical University, Taichung (TW); AXR Pharma Inc., Taipei (TW)

(72) Inventors: Yun-Lian Lin, Taipei (TW); Wei-Hsiang Hsu, Kaohsiung (TW); Young-Ji Shiao, Taipei (TW)

(73) Assignees: China Medical University, Taichung (TW); AXR Pharma Inc., Taipei (TW)

( * ) Notice: Subject to any disclaimer, the term of this patent is extended or adjusted under 35 U.S.C. 154(b) by 49 days.

(21) Appl. No.: 17/210,461

(22) Filed: Mar. 23, 2021

(65) Prior Publication Data

US 2021/0205399 A1 Jul. 8, 2021

Related U.S. Application Data

(62) Division of application No. 16/546,278, filed on Aug. 20, 2019, now abandoned.

(51) Int. Cl.
| | |
|---|---|
| *A61K 36/8988* | (2006.01) |
| *A61K 31/05* | (2006.01) |
| *A61K 31/11* | (2006.01) |
| *A61K 31/7034* | (2006.01) |
| *A61K 31/7076* | (2006.01) |
| *A61P 25/00* | (2006.01) |

(52) U.S. Cl.
CPC .......... *A61K 36/8988* (2013.01); *A61K 31/05* (2013.01); *A61K 31/11* (2013.01); *A61K 31/7034* (2013.01); *A61K 31/7076* (2013.01); *A61P 25/00* (2018.01)

(58) Field of Classification Search
None
See application file for complete search history.

(56) References Cited

U.S. PATENT DOCUMENTS

2007/0237840 A1* 10/2007 Chern ............... A61K 31/496
514/249

FOREIGN PATENT DOCUMENTS

CN 101143192 4/2011

OTHER PUBLICATIONS

Manavalan, A. et al. Gastrodia elata Blume (tianma) Mobilizes Neuroprotective Capacities. Int J Molecular Biology 3(2)219-241, 2012. (Year: 2012).*

Zuo, W. et al. Proliferation Enhancing Effects of Gastrodin on RSC96 Schwann Cells by Regulating ERK1/2 and P13K Signaling Pathways. Biomedicine & Pharmacotherapy 84:747-753, 2016. (Year: 2016).*
Identification of Phenolics and Nucleoside Derivatives in Gastrodia elata by HPLC-UV-MS. J Separation Science 30(10)1488-1495, Jul. 2007. (Year: 2007).*
Lin, Y. et al. Recent Research Progress on the Antidepressant Like Effect and Neuropharmacological Potential of Gastrodia elata Blume. Current Pharmacology Reports 4(3)220-237, 2018. (Year: 2018).*
Li, M. et al. Gastrodin Protects Neural Progenitor Cells Against Amyloid Beta Induced Neurotoxicity . . . J Molecular Neuroscience 60: 21-32, 2016. (Year: 2016).*
Tang, C. et al. Novel Strategies Using Total Gastrodin and Gastrodigenin, or Total Gastrodigenin for Quality Control of Gastrodia elata. Molecules 23: 1-11, 2018. (Year: 2018).*
Chen, J. et al. Design and Synthesis of Novel Dual Action Compounds Targetng the Adenosine A2a Receptor and Adenosine Transporter for Neuroprotection. ChemMedChem 6:1390-1400, 2011. (Year: 2011).*
Qiu C. et al. Post Stroke Gastrodin Treatment Ameliorates Ischemic Injury and Increases Neurogenesis . . . Brain Research 1712:7-15, Feb. 2019. (Year: 2019).*
Zhan, H. et al. The Rhizome of Gastrodia elata Blume . . . J of Ethnopharmacology 189:361-385, 2016. (Year: 2016).*
Huang, etl al. (Neuroprotective Principles from Gastrodia elata, J. Nat. Prod. 2007, 70, 571-574) (Year: 2007).*
Jang et al. (Neuropharmacological Potential of Gastrodia elata Blume and Its Components, Hindawi, Evidence-Based Complementary and Alternative Medicine, vol. 2015, 1-14) (Year: 2015).*
Hu et al. (Optimal Extraction Study of Gastrodin-Type Components from Gastrodia elata Tubers by Response Surface Design with Integrated Phytochemical and Bioactivity Evaluation, Molecules, 24(3), 547, Feb. 2019). (Year: 2019).*
Xie Miao, Shao Mingsha, Zhai Qingchao, Yu Hang, Guo Lei, Wei Yingqin, Li Yan, "Research Progress on Parishins from Gastrodia Elata", www.gdchem.com 2016 43(22): 93-95.
Guo Qinglong & Li Weidong, "Brief introduction of Human Anatomy and Physiology", pp. 22-23, published on Aug. 31, 2015, published by China Medical Science Press, published in China.
Chunlan Tang, Jialing Wang, Jie Yu, Li Wang, Mengchun Cheng, Wei Cui, Jinshun Zhao and Hongbin Xiao, "Identification, characterization and in vitro neuroprotection of N6-(4-hydroxybenzyl) adenine riboside and its metabolites",J. Nat. Prod. 2007, 70, 571-574.

(Continued)

*Primary Examiner* — Terry A McKelvey
*Assistant Examiner* — Jacob A Boeckelman
(74) *Attorney, Agent, or Firm* — Ying-Ting Chen

(57) ABSTRACT

The present invention relates to a composition and a method of utilizing *Gastrodia elata* extract or an adenosine analog to promote neurogenesis, wherein the *G. elata* extract includes gastrodin, gastrodigenin, parishins, $N^6$-(4-hydroxybenzyl) adenosine (T1-11) and 4-hydroxybenzaldehyde. The *G. elata* extract of the present invention exhibits anti-aging activity on nerve cells and can induce neurogenesis in mouse hippocampus.

2 Claims, 11 Drawing Sheets

(56) References Cited

OTHER PUBLICATIONS

Huang, li-ya, Ye si-ying and Liu Jie-shu, "The Comparison Between Radix Codonopsis Pilosulae and Gastrodia elata Blume on the Expression of Anti-oxidase of Aging Rat Induced by Haloperidol" Lishizhenmedicineandmateriamedicaresearch 2006 vol. 17 No. 9.

\* cited by examiner

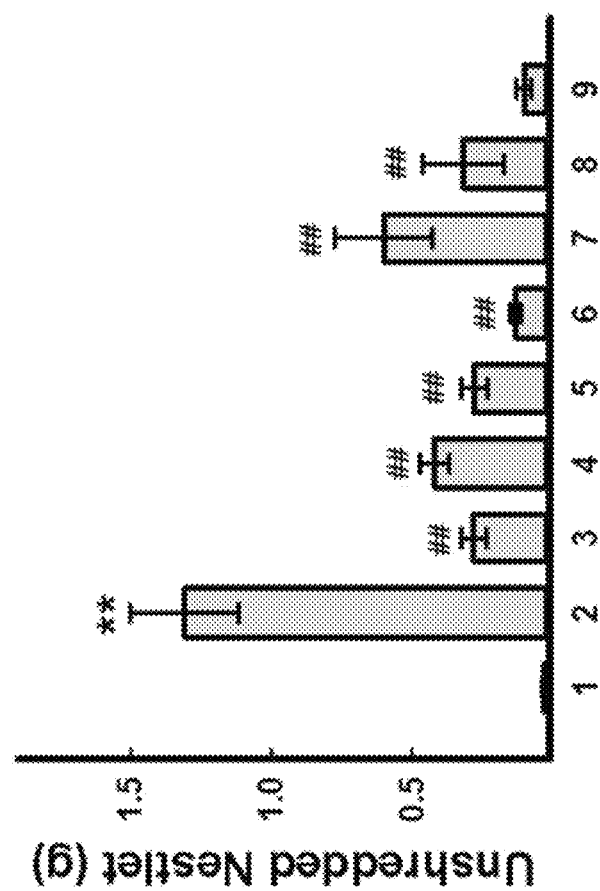
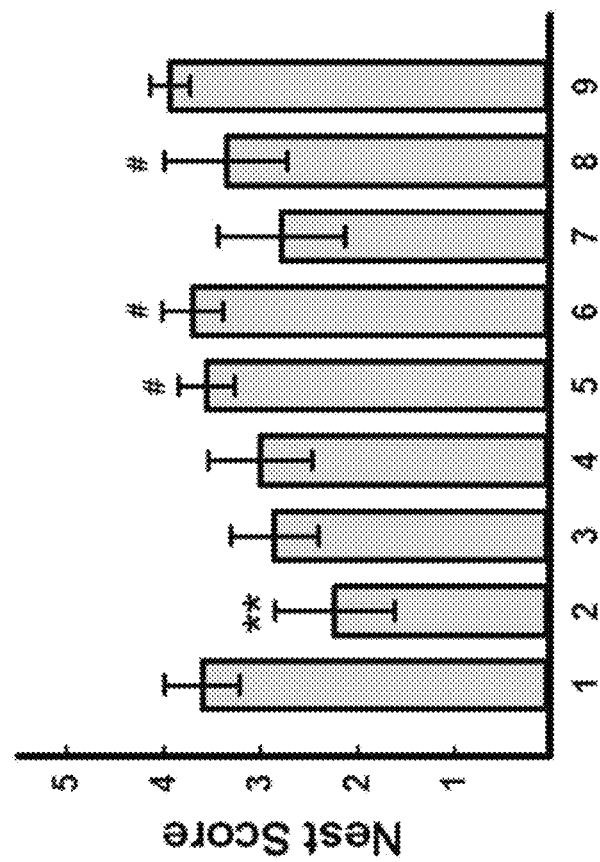
FIG. 5A
FIG. 5B

PHARMACEUTICAL COMPOSITION FOR PROMOTING NEUROGENESIS AND METHOD FOR PROMOTING NEUROGENESIS AND INHIBITING SENESCENCE OF BRAIN NEURONS

CROSS REFERENCE OF RELATED APPLICATION

This is a divisional application that claims the benefit of priority under 35 U.S.C. § 120 to a non-provisional application, application Ser. No. 16/546,278, filed Aug. 20, 2019, which is incorporated herewith by reference in its entirety.

BACKGROUND OF THE PRESENT INVENTION

Field of Invention

The present invention relates to a pharmaceutical composition and a method of utilizing Gastrodia elata extract or an adenosine analog to promote neurogenesis, wherein the G. elata extract includes gastrodin, gastrodigenin, parishins, $N^6$-(4-hydroxybenzyl) adenosine (T1-11) and 4-hydroxybenzaldehyde. The G. elata extract of the present invention exhibits anti-aging activity on nerve cells and induces neurogenesis in mouse hippocampus.

Description of Related Arts

Gastrodia elata Bl. (Tianma), the tubers of G. elata, is a perennial parasitic herb of Orchidaceae. It is used clinically to treat headache, dizziness, numbness, epilepsy and tetanus caused neurasthenia, vascular nerve headache and so on. Based on its clinical practice, there are many researches exploring its functions in preventing neurological damage. For example, gastrodin, a major compound in G. elata, was found to alter the metabolism of gamma amino butyric acid (GABA) in gerbil hippocampus (An, et al (2003)). Furthermore, an ether fraction of methanol extract of G. elata protected neuron against ischemia-induced injury in gerbils and also against kainic acid-induced neuronal damage in the mouse hippocampus (Kim, et al. (2001); Kim, et al. (2003)). The ether fraction of methanol extract of G. elata significantly reduced β-amyloid-induced neuronal cell death. Hsieh et al. demonstrated that administration of G. elata extract not only significantly reduced the number of seizures, but also delayed the onset time in kainic acid-induced epileptic seizures in rats (Hsieh, et al (2001)). The antiepileptic effect of G. elata was mediated by its regulating on free radical scavenging activity (Hsieh, et al. (2000)). Further, a methanolic extract of G. elata prevented serum-deprived PC12 cell apoptosis through suppression of c-Jun N-terminal kinase (JNK) activity (Huang, et al. (2004)).

SUMMARY OF THE PRESENT INVENTION

The main object of the present invention is to investigate the active ingredient or its composition of G. elata extract or adenosine analogs for promoting neurogenesis.

The present invention provides the pharmaceutical composition including G. elata extract or adenosine analog and further proves that the extract of G. elata or adenosine analog can promote neurogenesis.

The present invention provides a pharmaceutical composition for promoting neurogenesis, including: gastrodin, gastrodigenin, parishins, $N^6$-(4-hydroxybenzyl) adenosine (T1-11) and 4-hydroxybenzaldehyde.

In one embodiment, the parishins comprises parishin A, parishin B, parishin C or parishin E.

In one embodiment, a weight percentage of $N^6$-(4-hydroxybenzyl) adenosine is 0.5-4%, a weight percentage of gastrodin is greater than 25%, and a weight percentage of parishins is greater than 50%.

The present invention further provides a method of utilizing G. elata extract for promoting neurogenesis, the G. elata extract comprises gastrodin, gastrodigenin, parishin, $N^6$-(4-hydroxybenzyl) adenosine (T1-11) and 4-hydroxybenzaldehyde. In the present invention, the new born neurons are brain neurons.

The present invention further provides a method of utilizing isolated $N^6$-(4-hydroxybenzyl) adenosine (T1-11) or its pharmaceutical accepted salt for promoting neurogenesis. The new born neurons are hippocampal neurons.

Accordingly, the G. elata extract or $N^6$-(4-hydroxybenzyl) adenosine (T1-11) of the present invention exhibits anti-aging activity on nerve cells and can induce neurogenesis in mouse hippocampus.

These and other objectives of the present invention will no doubt become obvious to those of ordinary skill in the art after reading the following detailed description of the preferred embodiment that is illustrated in the various figures and drawings.

Significant difference between control and drug-treated cells is indicated by *p<0.05, **p<0.01, compare with control.

Figure 4B:
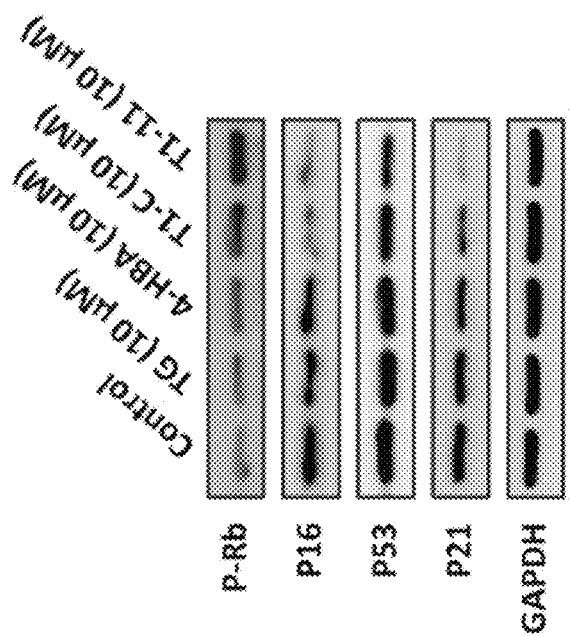
FIG. 4A shows the effect of G. elata extract TM1-2, $N^6$-(4-hydroxybenzyl) adenosine (T1-11), gastrodin (TG), other G. elata components (bis (4-hydroxybenzyl) sulfide T1-C), and gastrodigenin (4-HBA) of the pharmaceutical composition in the present invention, on cellular senescence markers, SA-β-gal activity, in SH-SYSY cells. Data are mean±SEM from at least four independent experiments.

FIG. 4B shows the effect of *G. elata* extract TM1-2, $N^6$-(4-hydroxybenzyl) adenosine (T1-11), gastrodin (TG), other *G. elata* components (bis (4-hydroxybenzyl) sulfide T1-C), and gastrodigenin (4-HBA) of the pharmaceutical composition in the present invention, on cellular senescence related molecules, phospho-Rb, p16, p53, and p21, in SH-SY5Y cells.

FIG. 5A shows the effect of *G. elata* extract TM1-2 and $N^6$-(4-hydroxybenzyl) adenosine (T1-11) of the pharmaceutical composition in the present invention on nesting. The nesting was performed after treatment. Group 1: Control; 2: D-galactose (200 mg/kg); 3: D-galactose (200 mg/kg)+Vit.E (100 mg/kg) (positive control); 4: D-galactose (200 mg/kg)+TM 1-2 (5 mg/kg); 5: D-galactose (200 mg/kg)+TM 1-2 (20 mg/kg); 6: D-galactose (200 mg/kg)+TM 1-2 (50 mg/kg); 7: D-galactose (200 mg/kg)+T1-11 (1 mg/kg); 8: D-galactose (200 mg/kg)+T1-11 (10 mg/kg); 9: T1-11 (10 mg/kg). Data are mean±SEM (n=6). Significant difference between control and D-gal-induced aging mice is indicated by **p<0.01 compared with the control group. Significant difference between the mice treated with D-gal alone and the mice treated with D-gal combined with TM1-2 or T1-11 is indicated by #p<0.05, compared with D-gal group.

FIG. 5B shows the effect of *G. elata* extract TM1-2 and $N^6$-(4-hydroxybenzyl) adenosine (T1-11) of the pharmaceutical composition in the present invention on the weight of the remaining unbroken cotton in the nest. The nesting was performed after treatment. Groups 1-9 of experiments are respectively described in FIG. 5A. Data are mean±SEM (n=6). Significant difference between control and D-gal-induced aging mice is indicated by **p<0.01 compared with the control group. Significant difference between the mice treated with D-gal alone and the mice treated with D-gal combined with TM1-2, Vit.E or T1-11 is indicated by ###p<0.01, compared with D-gal group.

Figure 6:
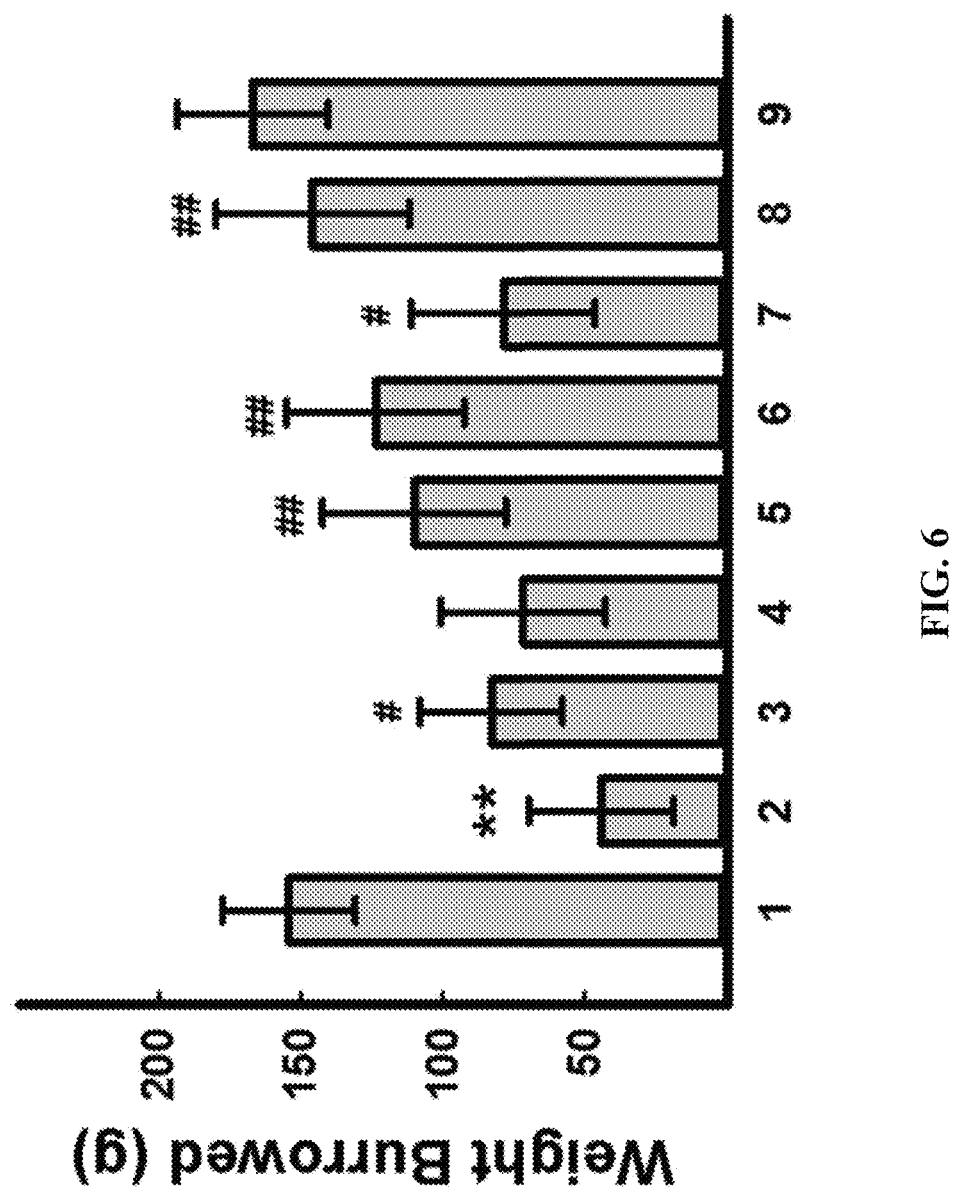

FIG. 6 shows the effect of *G. elata* extract TM1-2 and $N^6$-(4-hydroxybenzyl) adenosine (T1-11) of the pharmaceutical composition in the present invention, on ameliorating burrowing behavior impaired in D-gal-induced aging mice. The tasks of burrowing were performed after treatment. Groups 1-9 of experiments are respectively described in FIG. 5A. Data are mean±SEM (n=6). Significant difference between control and D-gal-induced aging mice is indicated by **p<0.01 compared with the control group. Significant difference between the mice treated with D-gal alone and the mice treated with D-gal combined with Vit.E or TM1-2 or T1-11 is indicated by #p<0.05, ###p<0.01, compared with D-gal group.

Figure 7B:
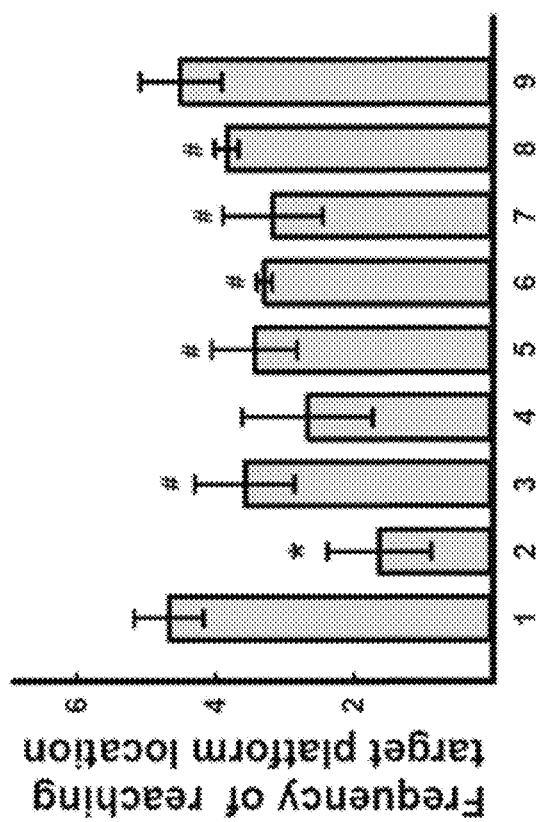
Figure 7A:
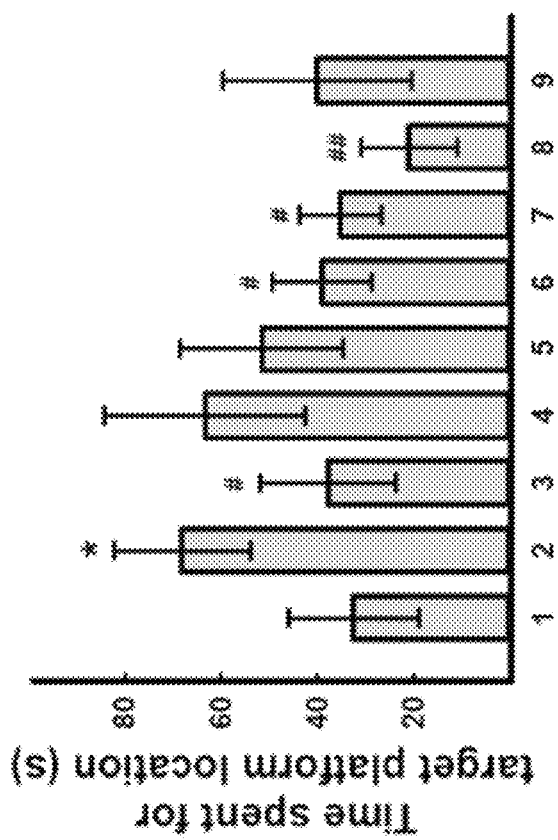

FIG. 7A shows the effect of *G. elata* extract TM1-2 and $N^6$-(4-hydroxybenzyl) adenosine (T1-11) of the pharmaceutical composition in the present invention on the escape latency time (sec) to reach the hidden platform during training session in D-gal-induced aging mice. For behavioral study, N=6 mice per group were used. Morris water maze was performed. Data shows the mean escape latency time (sec) to reach hidden platform during training session. Time spent in the target quadrant (where the platform was located during the hidden platform training session) during the probe test. Groups 1-9 of experiments are respectively described in FIG. 5A. Data are mean±SEM (n=6). Significant difference between control and D-gal-induced aging mice is indicated by *p<0.05 compared with the control group. Significant difference between the mice treated with D-gal alone and the mice treated with D-gal combined with Vit.E or TM1-2 or T1-11 is indicated by #p<0.05, ###p<0.01, compared with D-gal group.

FIG. 7B shows the effect of *G. elata* extract TM1-2 and $N^6$-(4-hydroxybenzyl) adenosine (T1-11) of the pharmaceutical composition in the present invention, on the number of platform crossings over the previous platform place during the probe test in D-gal-induced aging mice. Groups 1-9 of experiments are respectively described as above. Data are mean±SEM (n=6). Significant difference between control and D-gal-induced aging mice is indicated by *p<0.05 compared with the control group. Significant difference between the mice treated with D-gal alone and the mice treated with D-gal combined with Vit.E or TM1-2 or T1-11 is indicated by #p<0.05, compared with D-gal group.

Figure 8A:
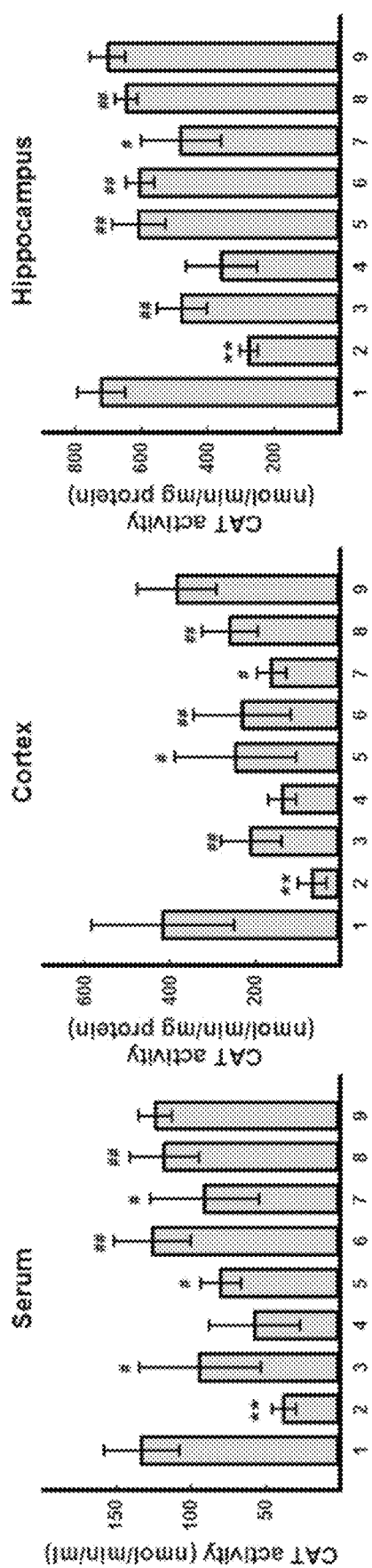

FIG. 8A shows the effect of *G. elata* extract TM1-2 and $N^6$-(4-hydroxybenzyl) adenosine (T1-11) of the pharmaceutical composition in the present invention, on the activity of catalase (CAT) in the serum, cortex, and hippocampus of D-gal-induced aging mice. Groups 1-9 of experiments are respectively described in FIG. 5A. Data are mean±SD (n=6). Significant difference between control and D-gal-induced aging mice is indicated by **p<0.01 compared with the control group. Significant difference between the mice treated with D-gal alone and the mice treated with D-gal combined with Vit.E or TM1-2 or T1-11 is indicated by #p<0.05, ###p<0.01, compared with D-gal group.

Figure 8B:
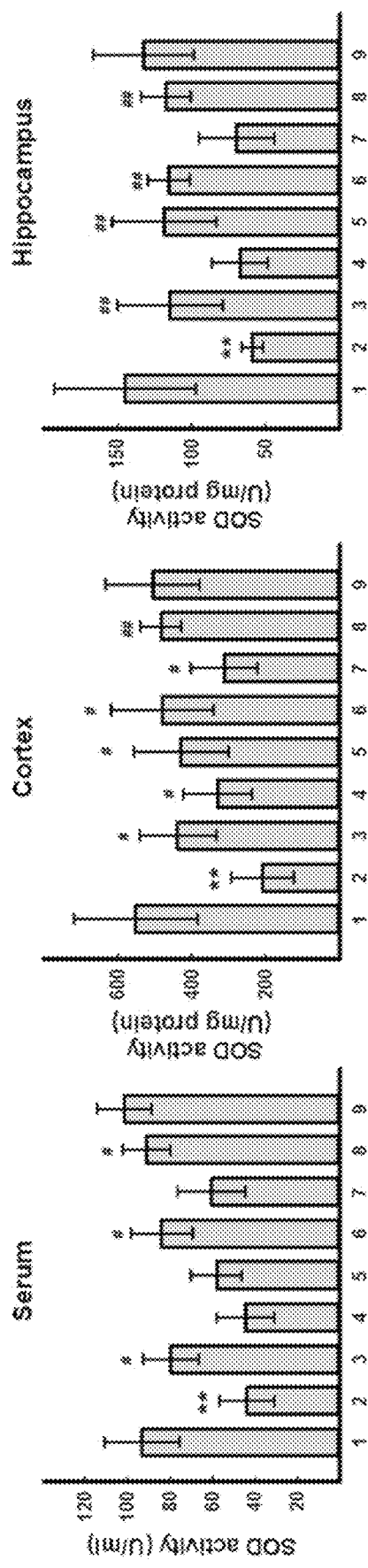

FIG. 8B shows the effect of *G. elata* extract TM1-2 and $N^6$-(4-hydroxybenzyl) adenosine (T1-11) of the pharmaceutical composition in the present invention, on the activity of superoxide dismutase (SOD) in the serum, cortex, and hippocampus of D-gal-induced aging mice. Groups 1-9 of experiments are respectively described in FIG. 5A. Data are mean±SD (n=6). Significant difference between control and D-gal-induced aging mice is indicated by **p<0.01 compared with the control group. Significant difference between the mice treated with D-gal alone and the mice treated with D-gal combined with Vit.E or TM1-2 or T1-11 is indicated by #p<0.05, ###p<0.01 compared with D-gal group.

Figure 9:
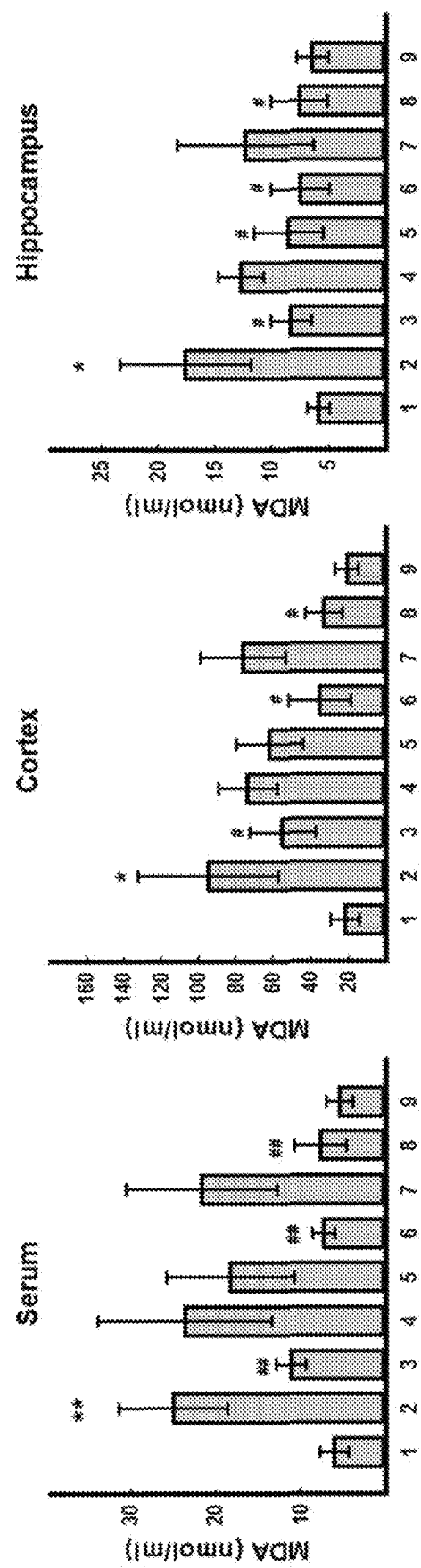

FIG. 9 shows the effect of *G. elata* extract TM1-2 and $N^6$-(4-hydroxybenzyl) adenosine (T1-11) of the pharmaceutical composition in the present invention, on lipid peroxidation (malondialdehyde) in the serum, cortex, and hippocampus of D-gal-induced aging mice. Groups 1-9 of experiments are respectively described in FIG. 5A. Data are mean±SD (n=6). Significant difference between control and D-gal-induced aging mice is indicated by *p<0.05, **p<0.01 compared with the control group. Significant difference between the mice treated with D-gal alone and the mice treated with D-gal combined with Vit.E or TM1-2 or T1-11 is indicated by #p<0.05, ###p<0.01, compared with D-gal group.

Figure 10A:
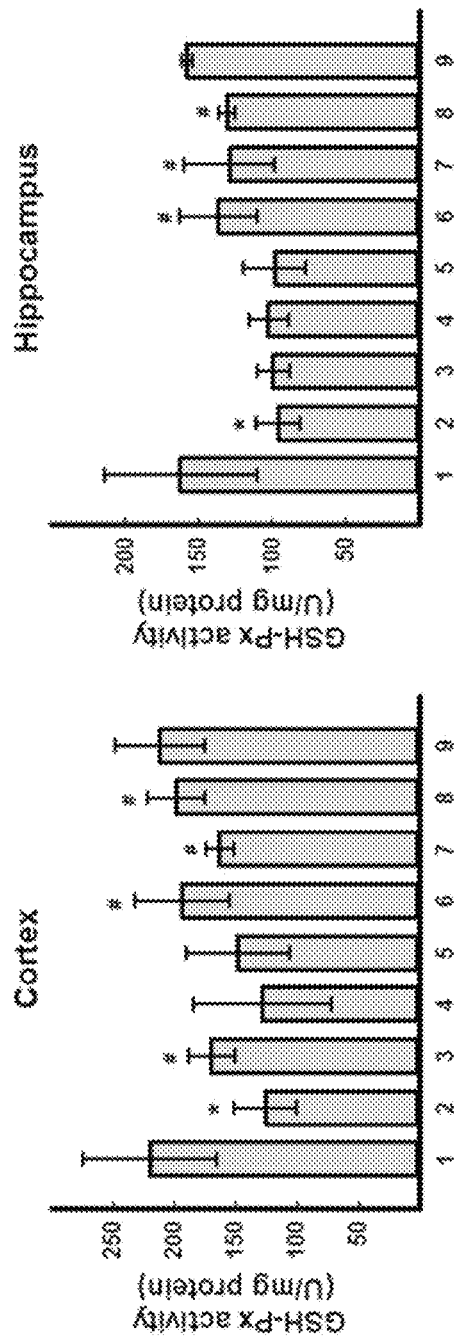

FIG. 10A shows the effect of *G. elata* extract TM1-2 and $N^6$-(4-hydroxybenzyl) adenosine (T1-11) of the pharmaceutical composition in the present invention, on the activity of glutathione peroxidase (GSH-Px) in the serum, cortex, and hippocampus of D-gal-induced aging mice. Groups 1-9 of experiments are respectively described in FIG. 5A. Data are mean±SD (n=6). Significant difference between control and D-gal-induced aging mice is indicated by *p<0.05 compared with the control group. Significant difference between the mice treated with D-gal alone and the mice treated with D-gal combined with Vit.E or TM1-2 or T1-11 is indicated by #p<0.05, compared with D-gal group.

Figure 10B:
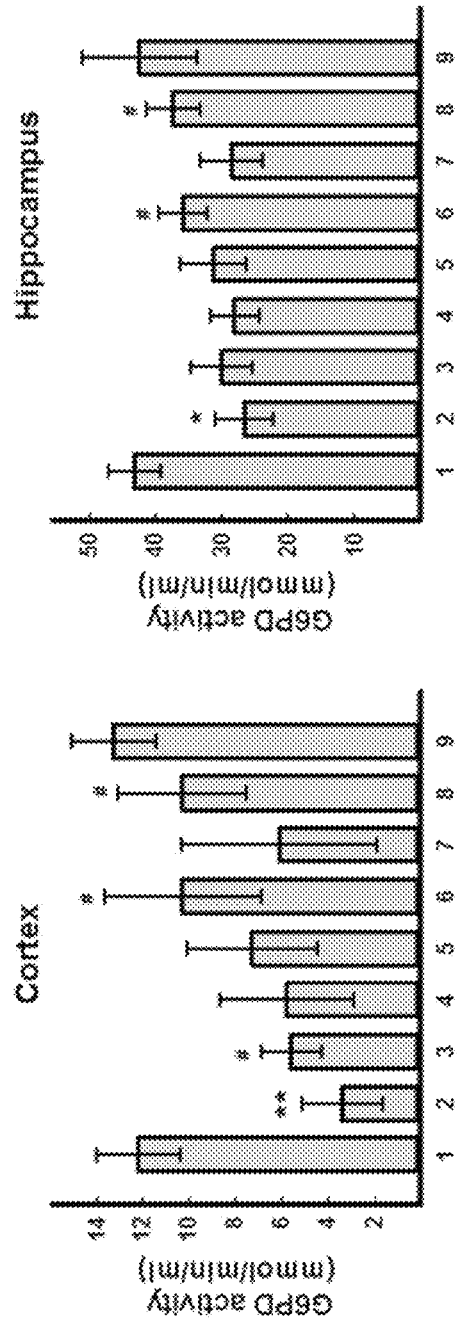

FIG. 10B shows the effect of *G. elata* extract TM1-2 and $N^6$-(4-hydroxybenzyl) adenosine (T1-11) of the pharmaceutical composition in the present invention, on the activity of glucose-6-phosphate dehydrogenase deficiency (G6PD) in the serum, cortex, and hippocampus of D-gal-induced aging mice. Groups 1-9 of experiments are respectively described in FIG. 5A. Data are mean±SD (n=6). Significant difference between control and D-gal-induced aging mice is indicated by *$p<0.05$, **$p<0.01$ compared with the control group. Significant difference between the mice treated with D-gal alone and the mice treated with D-gal combined with Vit.E or TM1-2 or T1-11 is indicated by #$p<0.05$ compared with D-gal group.

Figure 11A:
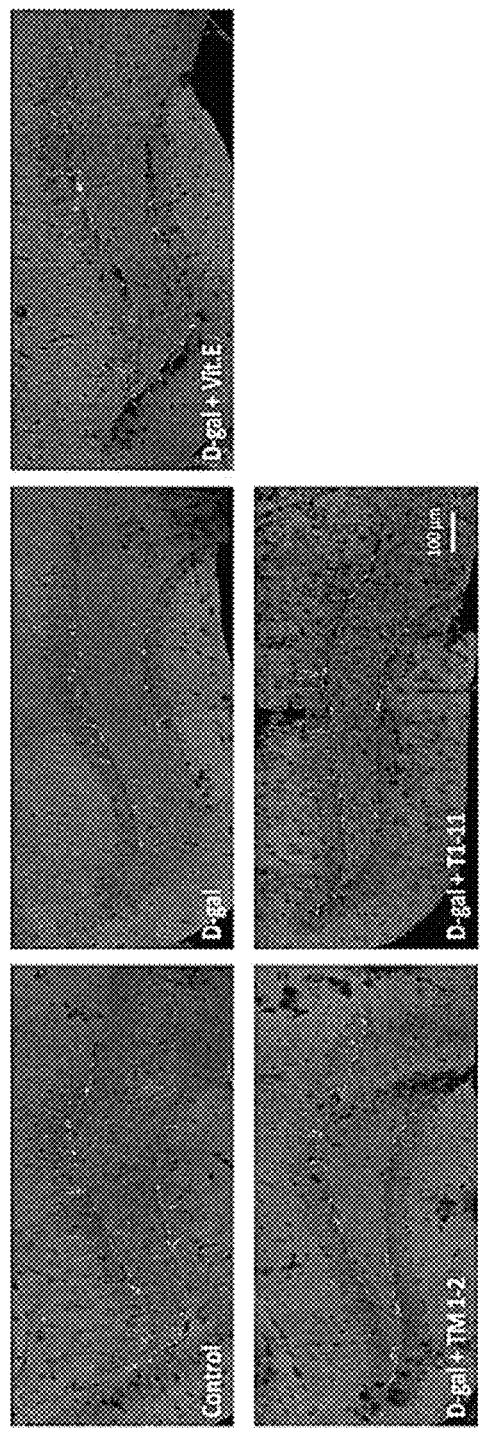

FIG. 11A shows the immunostaining images of the dentate gyrus area after treating *G. elata* extract TM1-2 and $N^6$-(4-hydroxybenzyl) adenosine (T1-11) of the pharmaceutical composition in the present invention and the effect on neurogenesis markers 5-bromo-2'-deoxy uridine (BrdU)) and doublecortin (DCX).

Figure 11B:
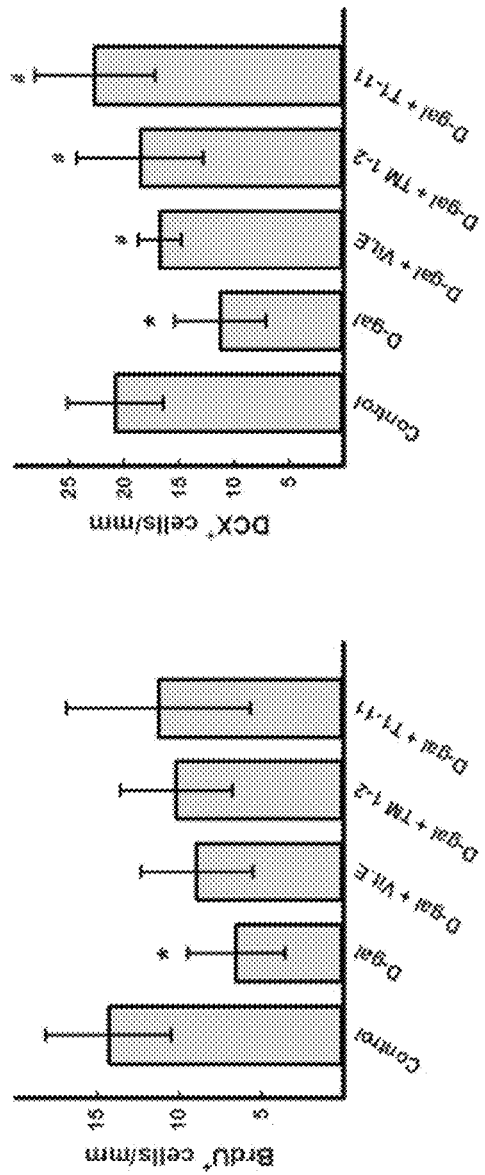

FIG. 11B shows the results of quantification of the immunostaining images of FIG. 11A. The number/mm subgranular zone (SGZ) of BrdU positive cells ($BrdU^+$) and DCX positive cells (DCX+) are counted. Significant difference between the mice treated with D-gal alone *$p<0.05$; and the mice treated with D-gal combined with Vit.E or TM1-2 or T1-11 is indicated by #$p<0.05$, compared with D-gal group.

DETAILED DESCRIPTION OF THE PREFERRED EMBODIMENT

The detailed description and technical contents of the present invention will now be described as follows:

The present invention is directed a pharmaceutical composition of promoting neurogenesis, including gastrodin, gastrodigenin, parishins, $N^6$-(4-hydroxybenzyl) adenosine (T1-11) and 4-hydroxybenzaldehyde. The parishins includes parishin A, parishin B, parishin C or parishin E. In the present invention, a weight percentage of $N^6$-(4-hydroxybenzyl) adenosine is 0.5-4%, a weight percentage of gastrodin is greater than 25%, and a weight percentage of parishins is greater than 50%.

The present invention further provides a method of utilizing *G. elata* extract for promoting neurogenesis, the *G. elata* extract comprises gastrodin, gastrodigenin, parishins, $N^6$-(4-hydroxybenzyl) adenosine (T1-11) and 4-hydroxybenzaldehyde. In the present invention, the new born neurons are brain neurons. In one embodiment, a weight percentage of $N^6$-(4-hydroxybenzyl) adenosine is 0.5-4%, a weight percentage of gastrodin is greater than 25%, and a weight percentage of parishins is greater than 50%.

The present invention further provides a method of utilizing isolated $N^6$-(4-hydroxybenzyl) adenosine (T1-11) or its pharmaceutical accepted salts for promoting neurogenesis. The new born neurons are brain neurons.

Example 1: Preparation of *G. elata* Extract

Commercially available cut pieces of *G. elata* tubers were extracted with an aqueous ethanol solution (70% ethanol, 50° C.) overnight. The crude extract was concentrated under reduced pressure to obtain a crude extract (TM 1). The concentrated sample was dried and then introduced into a macro-porous resin (DIAION HP20) column. TM1-1 was eluted by using water from the column and TM1-2 was then eluted by using 50% ethanol.

Example 2: High Performance Liquid Chromatography Analysis

The composition of TM1-2 obtained in Example 1 was then analyzed by a high-performance liquid chromatograph (HPLC) (Waters 2695). The analysis condition: Cosmosil 5C-18 AR-II, 4.6×250 mm column, UV 270 nm detector, a flow rate of 1.0 mL/min, mobile phase A: 0.01% phosphoric acid; B: acetonitrile; analysis flow: 0-15 min, 95-88% A; 15-30 min, 88% A; 30-40 min, 88-60% A. The results of the main components from HPLC analysis of the *G. elata* extract TM1-2 of the present invention are shown in FIG. 1.

Figure 1:
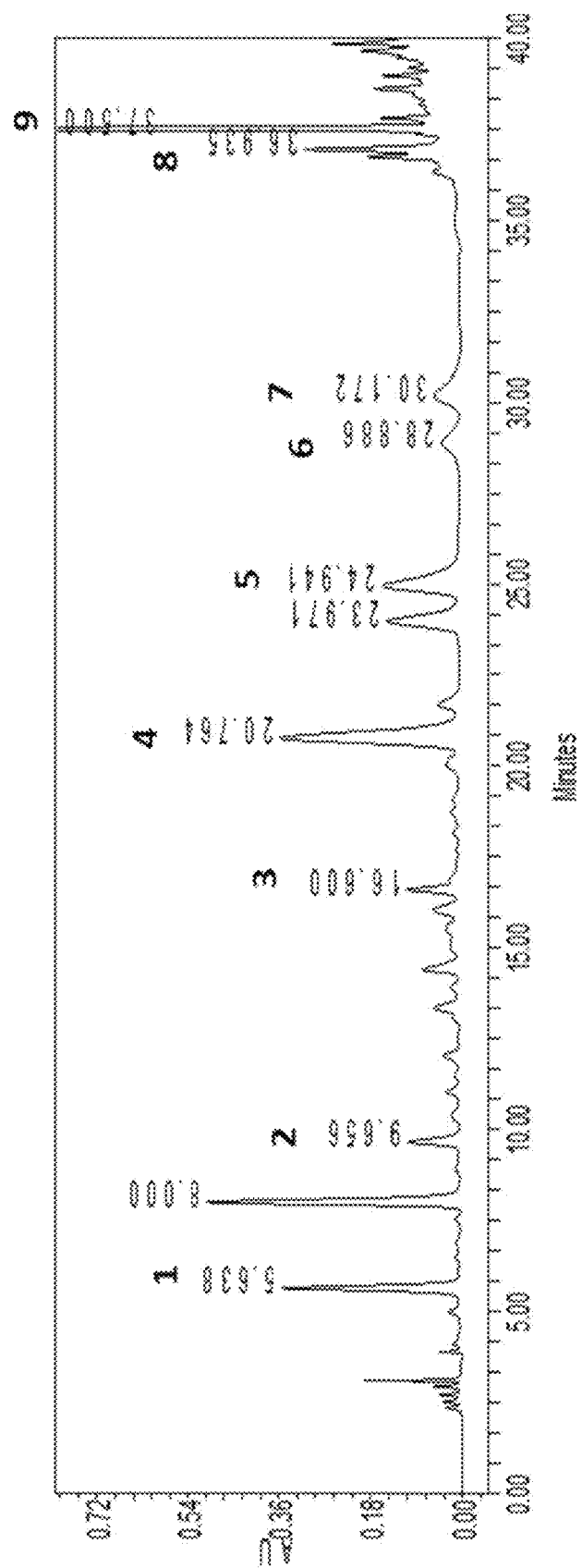
FIG. 1 shows the chemical profile of the HPLC analysis of G. elata extract TM 1-2 of the pharmaceutical composition for promoting neurogenesis in the present invention. The numerals in FIG. 1 indicate: 1: gastrodin; 2: p-hydroxybenzyl alcohol; 3: parishin E; 4: p-hydroxybenzyl aldehyde; 5: parishin B; 6: T1-11; 7: parishin C; 8: bis(4-hydroxybenzyl sulfone (T1-C); 9: parishin A.

As shown in FIG. 1, there are eight compounds appearing in HPLC result, respectively, gastrodin, gastrodigenin, parishin E, parishin B, parishin C, $N^6$-(4-hydroxybenzyl) adenosine (T1-11), parishin A and 4-hydroxybenzaldehyde, in which a weight percentage of $N^6$-(4-hydroxybenzyl) adenosine is 0.5-4%, a weight percentage of the parishins (including parishin A, parishin B, parishin C, parishin E) is greater than 50%, and a weight percentage of gastrodin is greater than 25%.

Example 3: Senescence Cell Culture

SH-SYSY cells (purchased from Taiwan and Bioresource Collection and Research Center (BCRC), 08C0066) was cultured in DMEM containing 10% fetal bovine serum, 100 U/ml penicillin and 100 µg/ml streptomycin in a carbon dioxide incubator. When SH-SYSY cells were grown in a 100 mm culture dish to a fullness of 80%, subculture was carried out. After about 20 subcultures, SH-SYSY cells began to show signs of senescence and show an increasing level of senescence-associated-β-galactosidase (SA-β-gal), significantly. Thus, the intracellular amount of SA-β-gal in the test cells were used as an indicator of cell senescence. These senescence cells were then used to perform the following aging-related cell experiments.

Figures 2A, 2B:
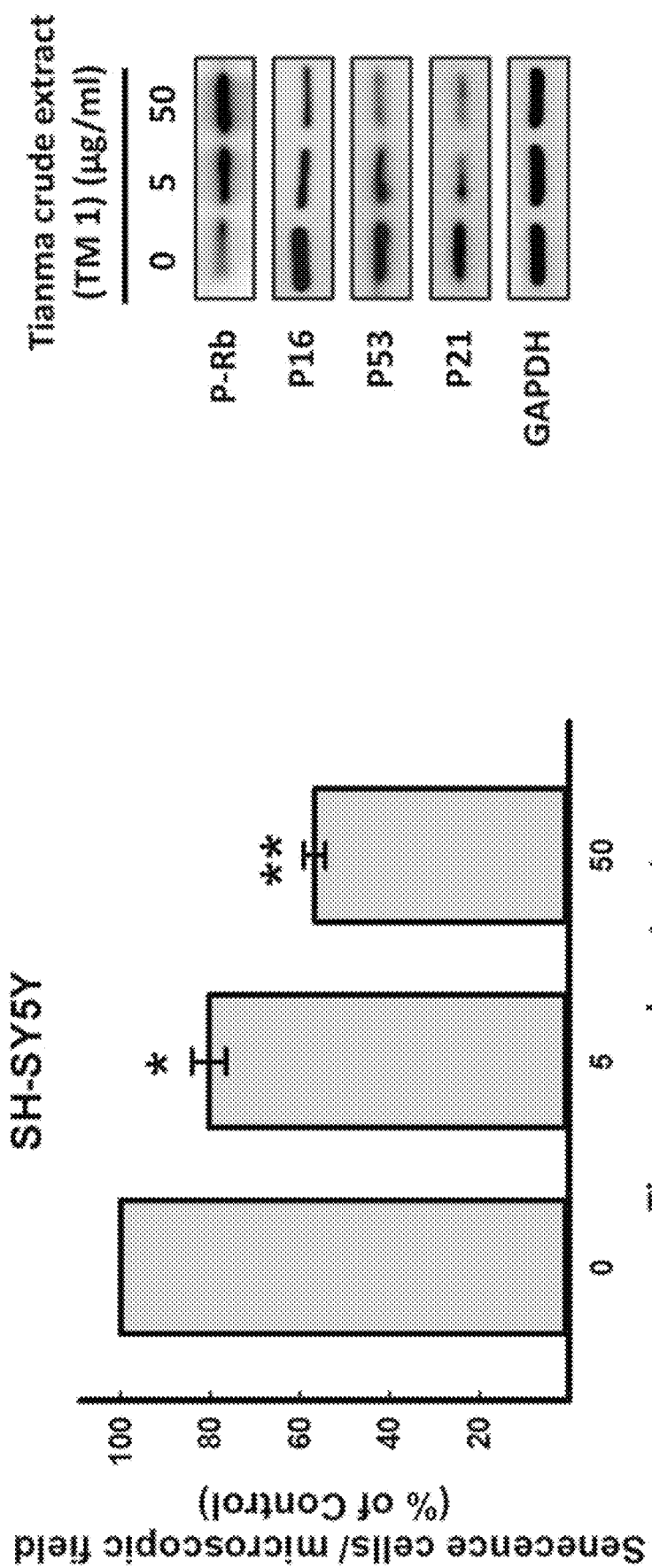
FIG. 2A shows the effect of G. elata crude extract (TM1) of the pharmaceutical composition for promoting neurogenesis in the present invention on cellular senescence markers, β-galactosidase (SA-β-gal) activity, in SH-SYSY cells. Data are mean±SEM from at least four independent experiments. Significant difference between control and drug-treated cells is indicated by *p<0.05, **p<0.01, compare with control.
FIG. 2B shows the effect of G. elata crude extract (TM1) of the pharmaceutical composition for promoting neurogenesis in the present invention on cellular senescence related molecules in SH-SYSY cells.
Figure 3B:
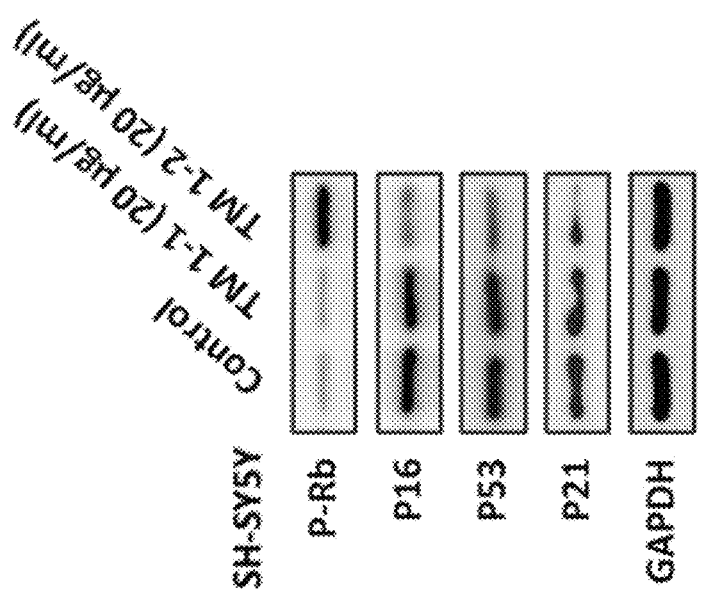
FIG. 3B shows the effect of G. elata extracts, TM1-1 and TM1-2 of the pharmaceutical composition in the present invention, on cellular senescence related molecules, phospho-Rb, p16, p53, and p21, in SH-SYSY cells.
Figure 3A:
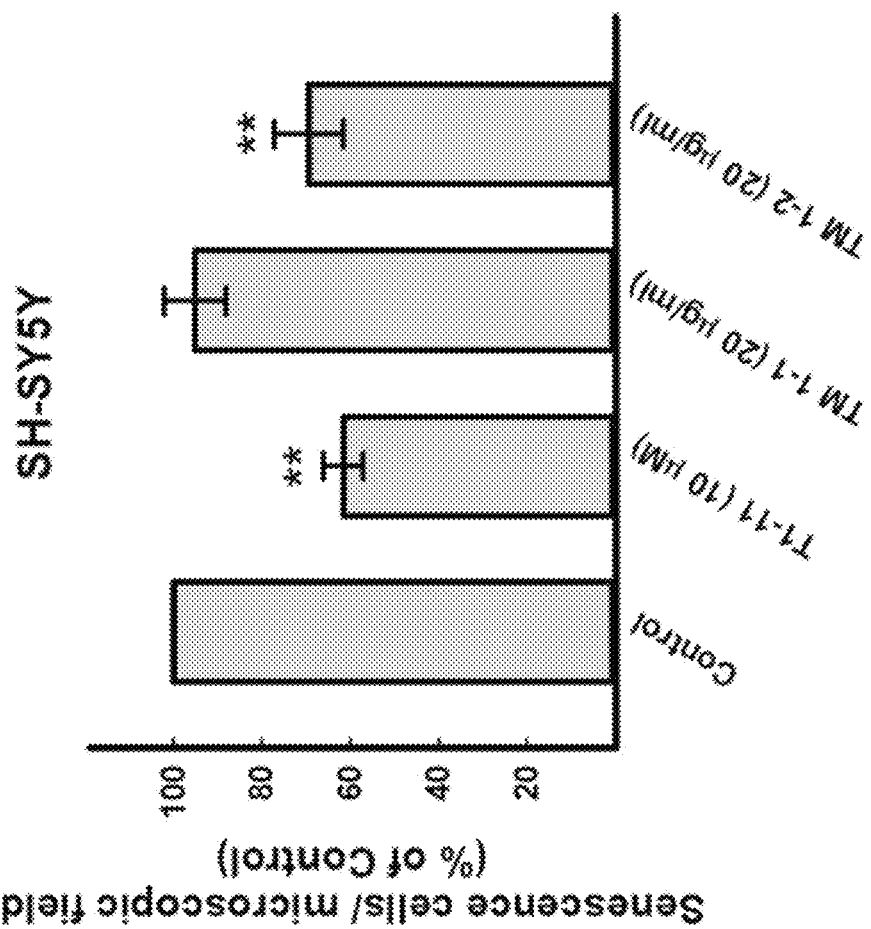
FIG. 3A shows the effect of G. elata extracts, TM1-1 and TM1-2 and $N^6$-(4-hydroxybenzyl) adenosine (T1-11) of the pharmaceutical composition in the present invention for promoting neurogenesis in the present invention on anti-aging activity in SH-SYSY cells. Data are mean±SEM from at least four independent experiments. Significant difference between control and drug-treated cells is indicated by **p<0.01, compare with control.
Figure 4A:
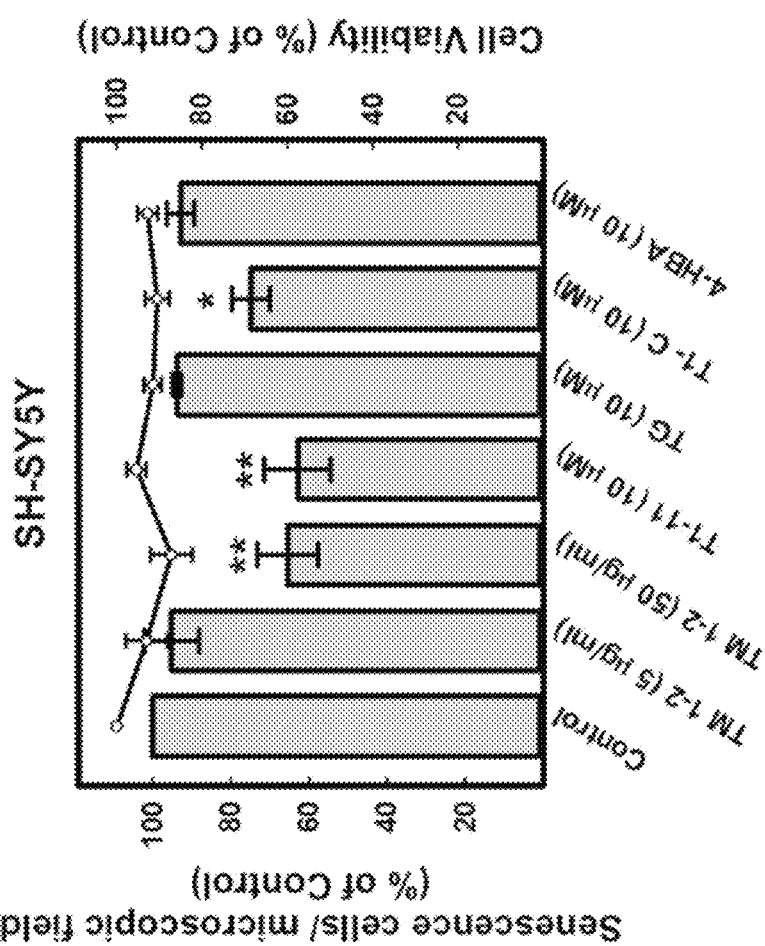

Example 4: *G. elata* Crude Extract TM1, *G. elata* Extract TM1-2 and Pure Compound $N^6$-(4-hydroxybenzyl) adenosine (T1-11) can Inhibit Cell Senescence The senescence SH-SYSY cells in embodiment 3 were treated with the *G. elata* crude extract TM1, the *G. elata* extract TM1-2 and $N^6$-(4-hydroxybenzyl) adenosine (T1-11) for 24 hours, then fixed with 4% formaldehyde, following by staining with SA-β-gal to evaluate the cell senescence level. The results (shown in FIG. 2A) show the *G. elata* crude extract TM1 can inhibit the production of intracellular SA-β-gal in SH-SYSY cells, and exhibit significant concentration-dependent effect. Secondly, the *G. elata* extract TM1-2 (FIG. 3A) and purified $N^6$-(4-hydroxybenzyl) adenosine (T1-11) (FIG. 3A and FIG. 4A) can also significantly reduce SA-β-gal in SH-SYSY cells. Furthermore, the mechanism of cell senescence is currently known to be driven by two independent pathways, p53-p21 pathway and p16-Rb pathway. Both p21 and p16 are cyclin-dependent kinase inhibitors (CDKI), which prevent Rb from being phosphorylated so as to inhibit Rb. Consequently, the activity of E2F transcription factors is inhibited and the cell cycle is therefore blocked. p53, p63 and p73 can directly induce the activation of p21 protein, leading to arrest in cell cycle and cellular senescence. The results of the present invention show that inhibition of p53, p16, p21 protein expression by *G. elata* extract TM1-2 and $N^6$-(4-hydroxybenzyl) adenosine (T1-11) can effectively postpone cell senescence (FIG. 2B, FIG. 3B, FIG. 4B).

Example 5: Evaluation of Behavior Pattern in Galactose Animal Model with *G. elata* Extract TM1-2 and $N^6$-(4-hydroxybenzyl) adenosine (T1-11)

In this embodiment, the effect of *G. elata* extract TM1-2 and purified $N^6$-(4-hydroxybenzyl) adenosine (T1-11) were tested on the behavior of galactose-induced senescence animal model.

A total of nine groups with 6 each animal experiments were conducted. The animals in groups 1-9 were: 1: blank control group, 2: D-galactose (0.3 g/kg), 3: D-galactose (0.3 g/kg)+vitamin E (100 mg/kg), 4: D-galactose (0.3 g/kg)+ TM1-2 low dose (5 mg/kg), 5: D-galactose (0.3 g kg)+ TM1-2 mid-dose group (20 mg/kg), 6: D-galactose (0.3 g/kg)+TM1-2 high dose group (50 mg/kg), 7: D-galactose (0.3 g/kg)+T1-11 low dose group (1 mg/Kg), 8: D-galactose (0.3 g/kg)+T1-11 high dose group (10 mg/kg), 9: T1-11 (10 mg/kg). D-galactose was treated by subcutaneous injection (0.3 g/kg body weight), and *G. elata* extract TM1-2, T1-11 and vitamin E were orally administrated (oral gavage). The test substances were treated once a day, continuing for 6 weeks. When administering, in addition to the blank control group, each group was continued to treat with 0.3 g/kg (body weight) D-galactose subcutaneously injected via back neck, and the blank control group was subcutaneously injected with physiological saline. The vitamin E group was used as a positive control group.

The results showed that both *G. elata* extract TM1-2 and $N^6$-(4-hydroxybenzyl) adenosine (T1-11) can effectively ameliorate the animal cognitive behavioral deficit of D-galactose-induced aging mice, including the construction of nests and burrowing. Since the aging mice are gradually losing these behavioral characteristics, these behavioral patterns can be used to evaluate the degree of aging.

In the Nesting Test (Deacon R (2012), Deacon RM (2006)), mice were given nesting materials, and they made nests in the corners of the cage and stayed in the nest. By using the nature of mouse nesting, nest cotton swabs were given, the scores of completing nesting were calculated, and the weight of the remaining unbroken cotton was weighed to assess the degree of mouse aging (FIGS. 5A and 5B).

In addition, since burrowing is normally spontaneous in mice, the burrowing test (Deacon R (2012)) was used to detect the degree of deterioration of burrowing behavior in mice (FIG. 6).

Furthermore, the memory learning ability of mice was evaluated using the Morris water maze test (Vorhees C V, et al. (2006)) (FIG. 7A and FIG. 7B).

As shown by the experimental results, *G. elata* extract TM1-2 and $N^6$-(4-hydroxybenzyl) adenosine (T1-11) can ameliorate cognitive behavioral deficit in D-galactose-induced aging in mice, and with the higher dose of *G. elata* extract TM1-2 and $N^6$-(4-hydroxybenzyl) adenosine (T1-11) have the better improvement.

Example 6: *G. elata* Extract TM1-2 and $N^6$-(4-hydroxybenzyl) adenosine (T1-11) Reduce Oxidative Damage in Blood and Brain Tissue of D-Galactose-Treated Animals After observing their behavior, the animals are intraperitoneally injected with 50 mg/g 5-bromo-2'-deoxyuridine (BrdU) continuously for one week. Then the animals were sacrificed to take their brain tissue and blood. The brain tissue was frozen, and a part of the tissue was used for the experiment of the present example, and the rest was sectioned for the experiment in Example 7. The blood was centrifuged to obtain serum for the following experiment.

Since aging is closely related to oxidative damage, the present embodiment further uses commercially available kit (provided by Cayman) for analyzing the activity of antioxidant enzymes including catalase (CAT), superoxide dismutase (SOD), lipid peroxide, glutathione peroxidase (GSH-Px) and glucose-6-phosphate dehydrogenase (G6PD) in the experimental animal blood and brain tissue.

It is demonstrated by the experimental results that *G. elata* extract TM1-2 and $N^6$-(4-hydroxybenzyl) adenosine (T1-11) significantly repaired the reduced activity of catalase (CAT) and superoxide dismutase (SOD) in serum, cortex and hippocampus and other brain tissue in the galactose-induced animals (FIG. 8A and FIG. 8B), as well as lipid peroxidation (malondialdehyde, MDA) (FIG. 9). Among them, groups 1-9 of the experiments were described in Example 5, respectively.

In addition, *G. elata* extract TM1-2 and $N^6$-(4-hydroxybenzyl) adenosine (T1-11) are also effectively reversed the level of glutathione peroxidation (GSH-Px) and glucose-6-phosphate dehydrogenase (G6PD) reduced by galactose (FIG. 10A and FIG. 10B). Among them, groups 1-9 of the experiments were described in Example 5, respectively.

Example 7: *G. elata* Extract TM1-2 and $N^6$-(4-hydroxybenzyl) adenosine (T1-11) Promote Neurogenesis in the Hippocampus of D-Galactose-Induced Mice After observing the behavior, the animals of Example 6 are intraperitoneally injected with 50 mg/g 5-bromo-2'-deoxyuridine (BrdU) continuously for a week. Then the animals were sacrificed and a part of the brain tissue is frozen and sectioned. The sections were immunohistochemically stained by first reacting with the first antibody, doublecortin (DCX) (purchased from Abcam) and then with a fluorescence-labeled secondary antibody (purchased from Jackson Labs Technologies, Inc). Thereafter, the sections were observed and photographed by a confocal microscope. Results showed that administrating *G. elata* extract (TM1-2) and $N^6$-(4-hydroxybenzyl) adenosine (T1-11) can ameliorate the reduced expression of BrdU and DCX in the hippocampus of D-galactose-induced mice (FIG. 11A and FIG. 11B).

The D-galactose-induced aging mice showed a significant decrease in BrdU and DCX-expressing cells in the hippocampus of the brain. This result is consistent with the Morris water maze test results in the previous Example 5, suggesting that galactose-induced aging mice lose the memory learning ability, while taking *G. elata* extract TM1-2 and $N^6$-(4-hydroxybenzyl) adenosine (T1-11) can ameliorate the aging phenomenon.

In light of the above experiments, the *G. elata* extract TM1-2 and purified $N^6$-(4-hydroxybenzyl) adenosine (T1-11) of the present invention can achieve the effect: (1) significant reducing the production of SA-β-gal which is corresponding to cellular senescence; (2) effectively improving the cognitive behavioral deficit caused by D-galactose-induced aging (nesting, burrowing and memory), wherein the improvement is in a dose-dependent manner; (3) significantly improving the reduced activities of SOD, CAT, GSH-Px and G6PD, and decreasing levels of lipid peroxide in blood and brain tissues of D-galactose-induced aging animals; and (4) ameliorating the D-galactose-induced BrdU and DCX cells decrease in the hippocampus. Accordingly, the pharmaceutical composition containing the *G. elata* extract (TM1-2) and $N^6$-(4-hydroxybenzyl) adenosine (T1-11) provided by the present invention may be effective in promoting neurogenesis, thereby ameliorate the aging phenomenon.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for inhibiting senescence of brain neurons of a subject, the method comprising:

administering an effective amount of a *Gastrodia elata* extract to the subject to increase amounts of antioxidant enzymes in the subject's brain and blood, wherein the *Gastrodia elata* extract comprises:

>50 wt % of parishin compounds;
   >25 wt % of gastrodin;
   gastrodigenin;
   0.5-4 wt % of $N^6$-(4-hydroxybenzyl) adenosine; and
   4-hydroxybenzaldehyde; and wherein the antioxidant enzymes comprise catalase (CAT), superoxide dismutase (SOD), glutathione peroxidase (GSH-Px), and glucose-6-phosphate dehydrogenase (G6PD); and wherein the *Gastrodia elata* extract is prepared by the steps of:

extracting pieces of *Gastrodia elata* tubers with a 70% aqueous ethanol solution at 50° C. overnight to obtain an extract solution;

concentrating and drying the extract solution to obtain a crude extract;

eluting the crude extract through a macro-porous resin column with 50% ethanol to obtain the *Gastrodia elata* extract.

2. The method of claim 1, wherein the parishin compounds comprises parishin A, parishin B, parishin C, and parishin E.

* * * * *